(12) United States Patent
Lee et al.

(10) Patent No.: US 10,314,533 B2
(45) Date of Patent: Jun. 11, 2019

(54) METHOD AND APPARATUS FOR RECOMMENDING A ROUTE

(71) Applicant: Samsung Electronics Co., Ltd., Gyeonggi-do (KR)

(72) Inventors: Jae-young Lee, Gyeonggi-do (KR); Cory Kim, Gyeonggi-do (KR); Sung-hyun Cho, Seoul (KR)

(73) Assignee: Samsung Electronics Co., Ltd (KR)

( * ) Notice: Subject to any disclaimer, the term of this patent is extended or adjusted under 35 U.S.C. 154(b) by 0 days.

(21) Appl. No.: 14/990,481

(22) Filed: Jan. 7, 2016

(65) Prior Publication Data

US 2016/0113565 A1 Apr. 28, 2016

Related U.S. Application Data

(63) Continuation-in-part of application No. 14/810,207, filed on Jul. 27, 2015, now Pat. No. 9,766,084, which
(Continued)

(30) Foreign Application Priority Data

Aug. 28, 2009 (KR) ........................ 10-2009-0080721

(51) Int. Cl.
*A61B 5/00* (2006.01)
*G01C 21/34* (2006.01)
(Continued)

(52) U.S. Cl.
CPC ............ *A61B 5/486* (2013.01); *A61B 5/0022* (2013.01); *A61B 5/02055* (2013.01); *A61B 5/0476* (2013.01); *A61B 5/4266* (2013.01); *A61B 5/4509* (2013.01); *A61B 5/4866* (2013.01); *G01C 21/20* (2013.01);
(Continued)

(58) Field of Classification Search
None
See application file for complete search history.

(56) References Cited

U.S. PATENT DOCUMENTS 5,842,145 A 11/1998 Zimmer
6,208,934 B1 3/2001 Bechtolsheim et al.
(Continued)

FOREIGN PATENT DOCUMENTS

EP 2 289 395 2/2011
JP 2005-305003 11/2005
(Continued)

OTHER PUBLICATIONS

Korean Office Action dated Aug. 3, 2015 issued in counterpart application No. 10-2009-0080721, 9 pages.
(Continued)

*Primary Examiner* — Lail A Kleinman
(74) *Attorney, Agent, or Firm* — The Farrell Law Firm, P.C.

(57) ABSTRACT

A method and an apparatus for recommending a route are provided. The route recommending method includes obtaining user's current body information; obtaining geographic information from a current position to a destination; and determining a recommended route to the destination on the basis of the body information and the geographic information.

16 Claims, 15 Drawing Sheets

Related U.S. Application Data is a continuation of application No. 12/871,404, filed on Aug. 30, 2010, now abandoned.

(51) Int. Cl.
  *G01C 21/20* (2006.01)
  *A61B 5/0476* (2006.01)
  *A61B 5/0205* (2006.01)

(52) U.S. Cl.
  CPC ..... *G01C 21/3415* (2013.01); *G01C 21/3484* (2013.01); *G01C 21/3407* (2013.01)

(56) References Cited

U.S. PATENT DOCUMENTS

| | | | |
|---|---|---|---|
| 6,256,579 | B1 | 7/2001 | Tanimoto |
| 6,470,267 | B1 | 10/2002 | Nozaki |
| 7,493,214 | B2 | 2/2009 | Jung et al. |
| 2002/0077749 | A1 | 6/2002 | Doi |
| 2002/0128773 | A1* | 9/2002 | Chowanic .......... G01C 21/3484 701/414 |
| 2006/0229809 | A1 | 10/2006 | Chen |
| 2007/0185644 | A1 | 8/2007 | Hirose |
| 2008/0009275 | A1 | 1/2008 | Werner et al. |
| 2008/0109121 | A1 | 5/2008 | Takeda |
| 2009/0291672 | A1 | 11/2009 | Treves et al. |
| 2010/0057346 | A1 | 3/2010 | Ehrlacher |
| 2010/0131148 | A1 | 5/2010 | Camhi et al. |
| 2010/0205060 | A1 | 8/2010 | Athsani et al. |
| 2010/0292914 | A1 | 11/2010 | Vepsalainen |
| 2011/0040193 | A1 | 2/2011 | Seppanen et al. |
| 2012/0078509 | A1* | 3/2012 | Choi .................. G01C 21/3461 701/423 |
| 2015/0081210 | A1* | 3/2015 | Yeh ..................... G06F 19/3406 701/428 |
| 2016/0209225 | A1* | 7/2016 | Nagy ................. G01C 21/3453 |

FOREIGN PATENT DOCUMENTS

| | | |
|---|---|---|
| JP | 2007-064797 | 3/2007 |
| JP | 2007-322249 | 12/2007 |
| JP | 2009-068861 | 4/2009 |
| KR | 1020060084093 | 7/2006 |

OTHER PUBLICATIONS

Korean Office Action dated Feb. 11, 2016 issued in counterpart application No. 10-2009-0080721, 9 pages.

* cited by examiner

FIG. 3

| | TOTAL DISTANCE (310) | DISTANCE ON UPHILL ROAD (320) | DISTANCE ON DOWNHILL ROAD (330) | NUMBER OF TRAFFIC LIGHTS (340) | OBSTACLES (350) | ROAD STATE (360) | DIFFICULTY (370) |
|---|---|---|---|---|---|---|---|
| WEIGHT | 1 | 2 | −2 | 1 | 2 | 1 | 1 |
| FIRST ROUTE (301) | 10(km) | 3(km) | 3(km) | TWO | ONE | 2(FAIR) | 17 |
| SECOND ROUTE (302) | 8 | 4 | 3 | 1 | 2 | 3(POOR) | 18 |
| THIRD ROUTE (303) | 12 | 2 | 6 | 2 | 0 | 1 | 7 |

FIG. 4

|  | ESTIMATED TIME (410) | ESTIMATED CALORIES (420) | NUMBER OF SELECTIONS (430) | RECOMMENDED RANKING (440) |
|---|---|---|---|---|
| FIRST ROUTE (301) | TWO HOURS | 800(kcal) | ONCE | SECOND |
| SECOND ROUTE (302) | 4 | 1600 | 4 | 2 |
| THIRD ROUTE (303) | 2.5 | 700 | 2 | 1 |

METHOD AND APPARATUS FOR RECOMMENDING A ROUTE

PRIORITY

This application is a Continuation-In-Part of U.S. patent application Ser. No. 14/810,207, filed on Jul. 27, 2015, which is a Continuation of U.S. application Ser. No. 12/871,404, filed on Aug. 30, 2010, which claims priority under 35 U.S.C § 119(a) from Korean Patent Application No. 10-2009-0080721, filed on Aug. 28, 2009, in the Korean Intellectual Property Office. The disclosure of each of the above-referenced applications is incorporated by reference in their entirety.

BACKGROUND

1. Field of the Invention

Methods, apparatuses, devices and computer readable recording mediums consistent with embodiments relate to a method and apparatus for recommending a route, and more particularly, to a route-recommending method and apparatus that dynamically changes a recommended route based on a user's body information and physical condition.

2. Description of the Related Art

Although the number of automobiles has increased rapidly, road networks have not been expanded and thus traffic jams are becoming more serious in many city areas. To avoid traffic jams and safely travel on unknown roads, route-guiding apparatuses with a Global Positioning System (GPS) function have been widely used.

Such route guiding apparatuses have been used not only by vehicle drivers but also by road walkers, hikers and cyclists.

SUMMARY OF THE INVENTION

The present invention has been made to address at least the above problems and/or disadvantages and to provide at least the advantages described below. Accordingly, an aspect of the present invention provides a method and an apparatus for recommending a route.

Embodiments provide a route recommending method including obtaining a user's current body information; obtaining geographic information from a current position to a destination; and determining a recommended route to the destination on the basis of the body information and the geographic information.

Determining the recommended route may further include a determination based upon user profile information including at least one of a user's past body information and route selection history information.

The route recommending method may further include updating the body information at some interval, and selectively changing the recommended route on the basis of the updated body information.

The route recommending method may further include, if an intersection exists within a certain range from the current position, updating the body information, and selectively changing the recommended route on the basis of the updated body information.

The route recommending method may further include receiving map data, and outputting map data showing the recommended route.

The route recommending method may further include receiving at least one of a signal for establishing a destination, a signal for establishing a target traveling time, and a signal for selecting a route.

Body information may include at least one of an electrocardiogram (ECG), brainwave, stress index, bone density index, body mass index, caloric consumption, and the user's age.

Geographic information may include at least one of the distance of a candidate route, the locations of support facilitates, the road conditions, the distance on uphill roads, the distance on downhill roads, and other obstacles.

The route recommending method may further include performing route guidance according to the recommended route.

Another embodiment provides a route recommending apparatus including a body information obtaining unit for obtaining a user's current body information, a geographic information obtaining unit for obtaining geographic information from a current position to a destination, and a route determining unit for determining a recommended route based upon body information and geographic information.

BRIEF DESCRIPTION OF THE DRAWINGS

The above and other aspects will become more apparent by describing in detail certain embodiments with reference to the attached drawings in which:

FIG. 3 illustrates a table including geographic information, according to an embodiment of the present invention;

FIG. 4 illustrates a table showing a candidate route list, according to an embodiment of the present invention;

DETAILED DESCRIPTION

Figure 1:
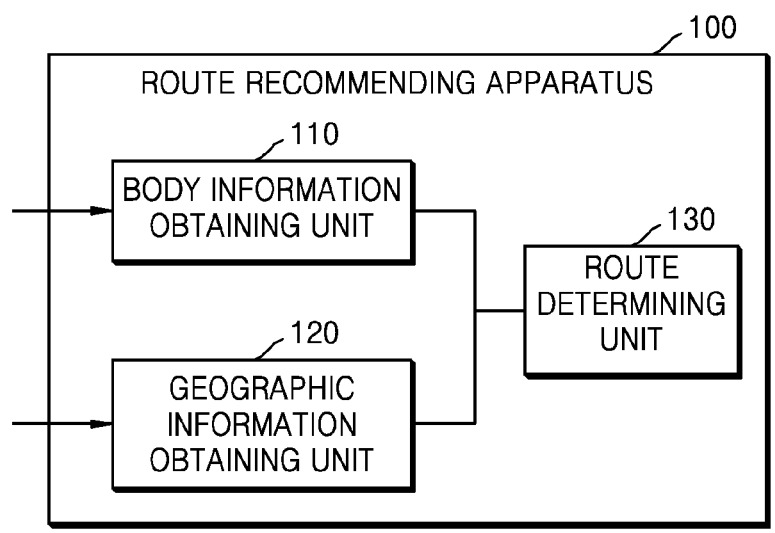
FIG. 1 is a block diagram illustrating a route recommending apparatus, according to an embodiment of the present invention.

Embodiments of the present invention are described in detail with reference to the accompanying drawings. The same or similar components may be designated by similar reference numerals although they are illustrated in different drawings. Detailed descriptions of constructions or processes known in the art may be omitted to avoid obscuring the subject matter of the present invention.

FIG. 1 illustrates a route recommending apparatus 100, according to an embodiment of the present invention.

The route recommending apparatus 100 according to an embodiment of the present invention may include a body information obtaining unit 110, a geographic information obtaining unit 120, and a route determining unit 130. The route recommending apparatus 100 may be installed in the form of a hardware or software module inside a portable apparatus, which includes for example, a mobile phone.

The body information obtaining unit 110 obtains a user's current body information. The body information may include any information related to the user's physical condition. For example, the body information may include blood pressure, electrocardiogram (ECG), heart rate, skin temperature, breath condition, weight, height, body motion, electromyogram, perspiration, and/or skin conductivity.

The body information obtaining unit 110 may update the user's current body information in real time or update the user's current body information whenever a predetermined condition is satisfied. A method of establishing the predetermined condition may vary. For example, the body information obtaining unit 110 may update the user's current body information whenever a predetermined period of time elapses or when a user approaches a nearby intersection. As described herein, updating the user's current body information means that the body information obtaining unit 110 re-obtains the user's body information. The term "intersection" means a point where at least two routes cross each other. When a user approaches the intersection, the body information obtaining unit 110 updates the user's body information so that route determining unit 130 (to be described later) determines the route to be selected from the intersection.

The geographic information obtaining unit 120 obtains geographic information from a current position to a destination. The geographic information obtaining unit 120 may obtain geographic information about each route that can be used to reach a destination from the user's current position. The geographic information may include any information related to topography or geography, such as position of a route, total length of a route, an uphill distance on a road, a downhill distance on a road, road conditions, the number of route facilities including crosswalks, etc. The geographic information may be obtained from an external apparatus or a GPS module that is connected to the route recommending apparatus 100 via a network, or may be stored in the route recommending apparatus 100.

The route determining unit 130 determines a recommended route to the destination on the basis of body information and geographic information. The route determining unit 130 may search all possible routes that can be used to reach the destination from the current position, and may determine a recommended route that is the most appropriate route for a user in view of the body information.

The route determining unit 130 may also determine a recommended route on the basis of a user's profile information. The user profile information may include any information related to a user, for example, past body information, fitness history, medical history, preferred route, etc. The user profile information may be stored in the route recommending apparatus 100 or received from the outside via a network. The route recommending apparatus 100 may include a plurality of items of user profile information corresponding to each of a plurality of users. The recommended route determining unit 130 may determine which profile information to use on the basis of user's body information or a user's input.

After the body information obtaining unit 110 updates the body information, the route determining unit 130 selectively determines whether to change the recommended route. If the body information is updated in real time, the route determining unit 130 may determine whether to change the recommended route only when variation of the body information is greater than a threshold value. If the body information is updated at a predetermined time interval or if the body information is updated when a distance difference between the user and an intersection is less than the threshold value, the route determining unit 130 may determine whether to change the recommended route whenever new body information is presented.

If the recommended route has changed, the route determining unit 130 may inform the user through a sound or vibration that indicate that the recommended route has been changed.

In addition to the route determining unit 130, a route guiding unit (not shown) may perform route guidance without a user's input. The route guiding unit may even display a candidate route list so that a user may directly select the recommended route. In this case, the candidate route list may show the recommended route. If the user selects the recommended route from the candidate route list, the route guiding unit may guide the user along the recommended route. On the other hand, if the user selects another route, the route guiding unit may guide the user along the selected route.

Figure 2:
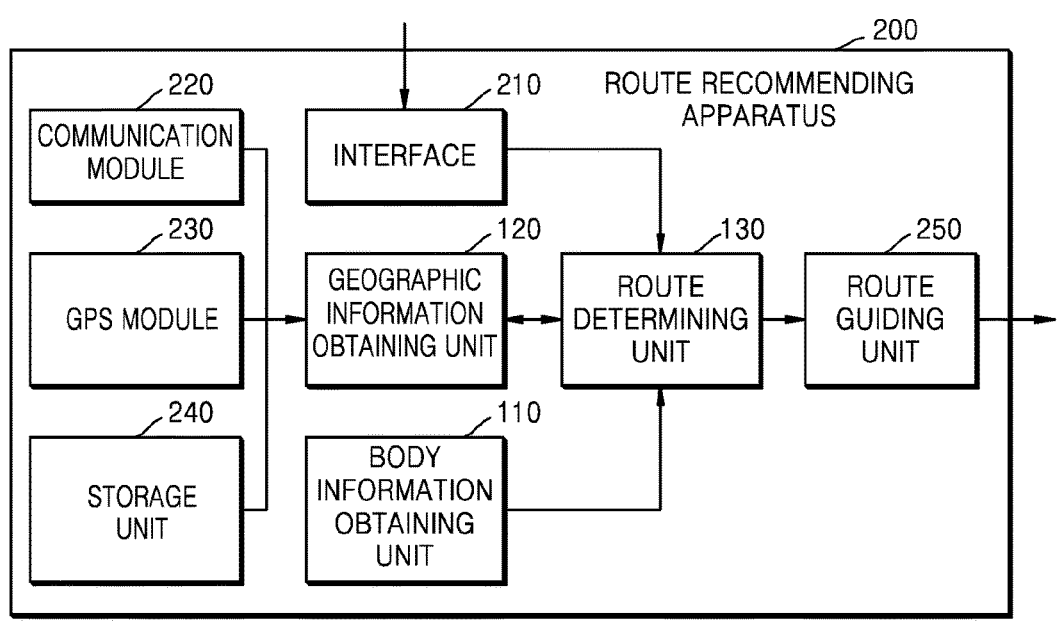
FIG. 2 is a block diagram illustrating a route recommending apparatus, according to another embodiment of the present invention.

FIG. 2 illustrates a route recommending apparatus 200, according to another embodiment of the present invention.

The route recommending apparatus 200 may include an interface 210, a body information obtaining unit 110, a geographic information obtaining unit 120, a route determining unit 130, a communication module 220, a GPS module 230, a storage unit 240, and a route guiding unit 250. The body information obtaining unit 110, the geographic information obtaining unit 120, and the route determining unit 130 that are included in the route recommending apparatus 200 may perform the same functions as those described with respect to FIG. 1.

The interface 210 receives an input signal from the outside. For example, the interface 210 may receive a destination and a target traveling time that are input by a user, or may receive a route selected by the user.

The communication module 220 may receive map data, geographic information or information about other users' preferred routes from a wired or wireless network.

The GPS module 230 may receive location information from a GPS server or satellite network.

The storage unit 240 may store at least one of a user's profile information, map data, and geographic information.

The route guiding unit 250 may perform route guidance according to the selected route.

Hereinafter, sequential operations of the route recommending apparatus 200 will be described.

First, a user inputs a destination through the interface 210. The user may also input a target time to the destination.

The body information obtaining unit 110 obtains the user's current body information. The body information obtaining unit 110 preferably directly obtains the user's body information through a sensor or sensor network.

The geographic information obtaining unit 120 obtains geographic information about a current position, the destination, and all points in-between. The geographic information obtaining unit 120 may obtain the geographic information from the communication module 220, the GPS module 230, or from the storage unit 240.

Next, the route determining unit 130 determines a recommended route on the basis of the geographic information, body information and user input. As described above, the route determining unit 130 may also determine the recommended route on the basis of user profile information.

The route determining unit 130 provides a candidate route list to a user. The candidate route list may show the recommended route.

The user selects any one of the candidate routes shown in the candidate route list through the interface 210.

The route guiding unit 250 performs route guidance according to the selected route. The route guiding unit 250 may output map data to a display apparatus, or may inform a user of a crossroad or a dangerous area through a sound or vibration indicator.

While the route guiding unit 250 performs route guidance, if the user approaches an intersection, the body information obtaining unit 210 updates body information.

The route determining unit 130 determines whether to change the recommended route on the basis of the updated body information. For example, when the user's heart rate suddenly changes or when the user's body temperature increases greater than a threshold value, or when the amount of sweat produced is greater than a threshold value, the route determining unit 130 may determine that the user is not fit to use the route. Accordingly, the route determining unit 130 may change the route to a new route, which includes better road conditions such as flat or downhill roads, as a recommended route.

According to an embodiment, if the user approaches an intersection, the route determining unit 130 may inform a user in advance through sound or vibration that the recommended route may be changed.

FIG. 3 illustrates geographic information, according to an embodiment of the present invention.

In FIG. 3, the geographic information corresponding to each candidate route is shown. The geographic information includes information about, for example, a total distance 310 from a current position to a destination, a distance on an uphill road 320, a distance on a downhill road 330, the number of traffic lights 340, existence and number of any obstacles 350, and the road state 360. In addition, the geographic information may include any information related to topography or geography.

The recommended route determining unit 130 may determine the difficulty of each route on the basis of the geographic information. In this case, a different weight may be applied to each item. In FIG. 3, it is assumed that a weight '1' is applied to the total distance 310, the number of traffic lights 340, and the road state 350, a weight '2' is applied to the obstacle 350, and a weight '−2' is applied to the distance of a downhill road 330.

In this case, the difficulty 370 of a first route 301 satisfies the equation $(11*1)+(3*2)+(3*(-2))+(2*1)+(1*2)+(2*1)=17$, the difficulty 370 of a second route 302 satisfies the equation $(8*1)+(4*2)+(3*(-2))+(1*1)+(2*2)+(3*1)=18$, and the difficulty 370 of a third route 303 satisfies the equation $(12*1)+(2*2)+(6*(-2))+(2*1)+(0*2)+(1*1)=7$. That is, it is most difficult to reach the destination along the second route 302, and it is least difficult to reach the destination along the third route 303. The above-mentioned method of calculating route difficulty is just an example, and thus difficulties of candidate routes may be calculated by additionally using other information or other mathematical relationships.

The recommended route determining unit 130 may determine a route which is the most suitable for a user on the basis of such difficulty information and the user's current body information.

FIG. 4 illustrates a candidate route list according to an embodiment of the present invention.

The candidate route list according to an embodiment of the present invention includes estimated time information 410, estimated calories information 420, a number of selections information 430, and recommended ranking information 440. In addition, the candidate route list may include any information that may be relevant to a user's selection.

The estimated time information 410 is the estimated time for arriving at a destination via a candidate route.

The estimated calories information 420 is the estimated calories consumed by a user when he arrives at the destination via a candidate route.

The number of selections information 430 is the number of times a user has selected a candidate route in the past.

The recommended ranking information 440 is the ranking of a candidate route according to another user's recommendation. In this case, the recommended ranking information 440 may be based upon route information recommended by a user in a group having information similar to the user of the route recommending apparatus 100.

The candidate route list may be produced using data from a user's profile. For example, if a history of selecting the candidate route exists, the user's profile may include information about time the taken and the calories consumed when using the specific candidate route. When the user selects the same destination, the candidate route list may be generated on the basis of the user's profile.

The recommended route determined by the route determining unit 130 is shown in the candidate route list. If the route determining unit 130 determines that the user is physically fit and that a target traveling time entered by the user corresponds with the estimated time information 410 of the second route 302, the route determining unit 130 may determine the second route 302 is the recommended route. In FIG. 4, the recommended route is shown as a highlighted line so that the user may easily recognize it.

A recommendation route may be determined based on user's preferences. As an example, if the user wants a fastest route, the fastest route (301) is determined as a recommendation and if the user wants a hardest route, the hardest route (302) is determined as a recommendation.

Figure 5:
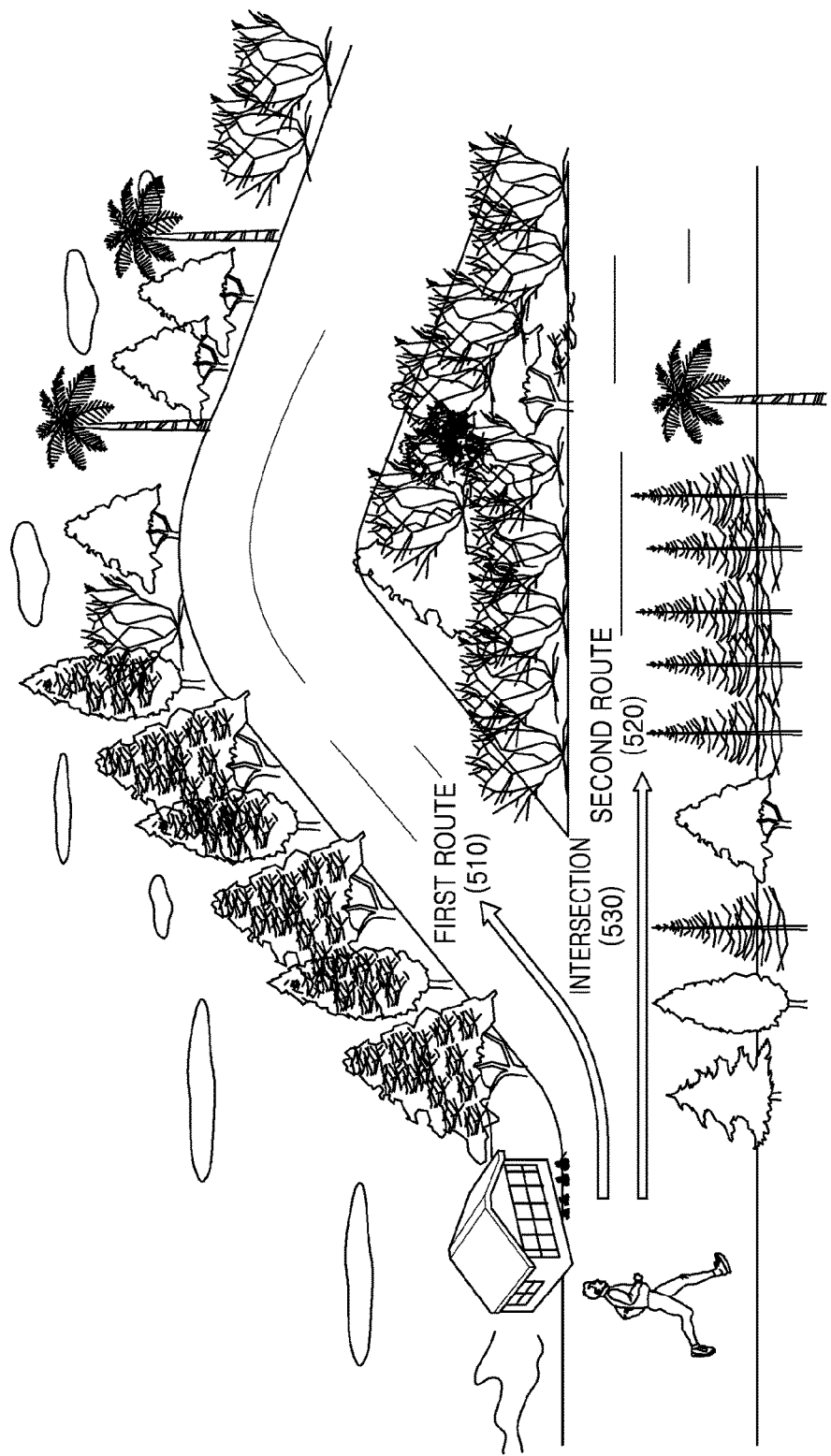
FIG. 5 is a diagram which illustrates a method of changing a recommended route using a route recommending apparatus, according to an embodiment of the present invention.

FIG. 5 illustrates a method of changing a recommended route in the route recommending apparatus 100, according to an embodiment of the present invention.

First, when a user operates the route recommending apparatus 100, the route recommending apparatus 100 obtains the user's current body information and determines a recommended route based upon such information. Since a first route 510 is a hiking trail having many uphill roads, when a user uses the first route 510, the user may burn many calories. On the other hand, if the user selects the second route 520, he may use less energy because the terrain is easier. It is assumed now that the route recommending apparatus 100 determines the first route 510 as a recommended route.

The route recommending apparatus 100 begins route guidance according to the first route 510. The user approaches an intersection 530 while jogging along the first route 510. In this case, the route recommending apparatus

100 updates the user's body information and determines whether to change the recommended route on the basis of the updated body information. For example, if the route recommending apparatus 100 determines that the user overexerted himself on the basis of a his heart rate and body temperature, the route recommending apparatus 100 may change the recommended route from the first route 510 to the easier second route 520. On the other hand, if the route recommending apparatus 100 determines that the user used less energy on the basis of a user's heart rate and body temperature, the route recommending apparatus 100 may not change the recommended route. The route recommending apparatus 100 continues route guidance according to the first route 510.

Figure 6:
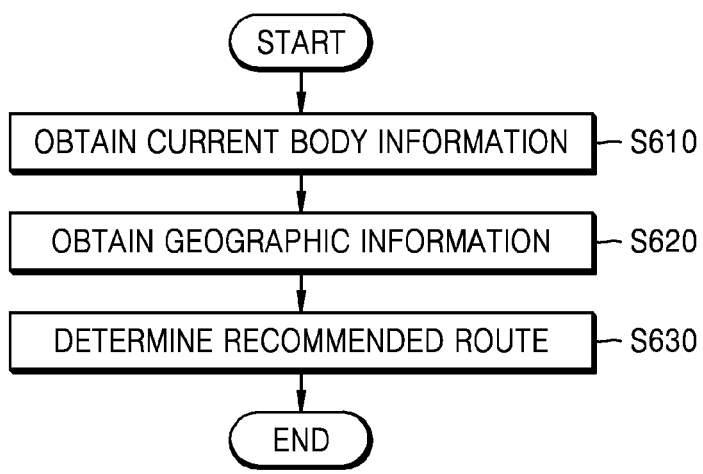
FIG. 6 is a flowchart illustrating a method of recommending a route, according to an embodiment of the present invention.

FIG. 6 illustrates a method of recommending a route, according to an embodiment of the present invention.

In step s610, the user's current body information is obtained.

In step s620, geographic information from a current position to a destination is obtained.

In step s630, a recommended route is determined on the basis of the body information and the geographic information. The recommended route may also be determined on the basis of user profile information including at least one of the user's past body information and route selection history information.

Afterwards, the body information is updated at a predetermined time interval or when a user approaches an intersection from within a critical distance. The recommended route may be selectively changed on the basis of the renewed body information.

Figure 7:
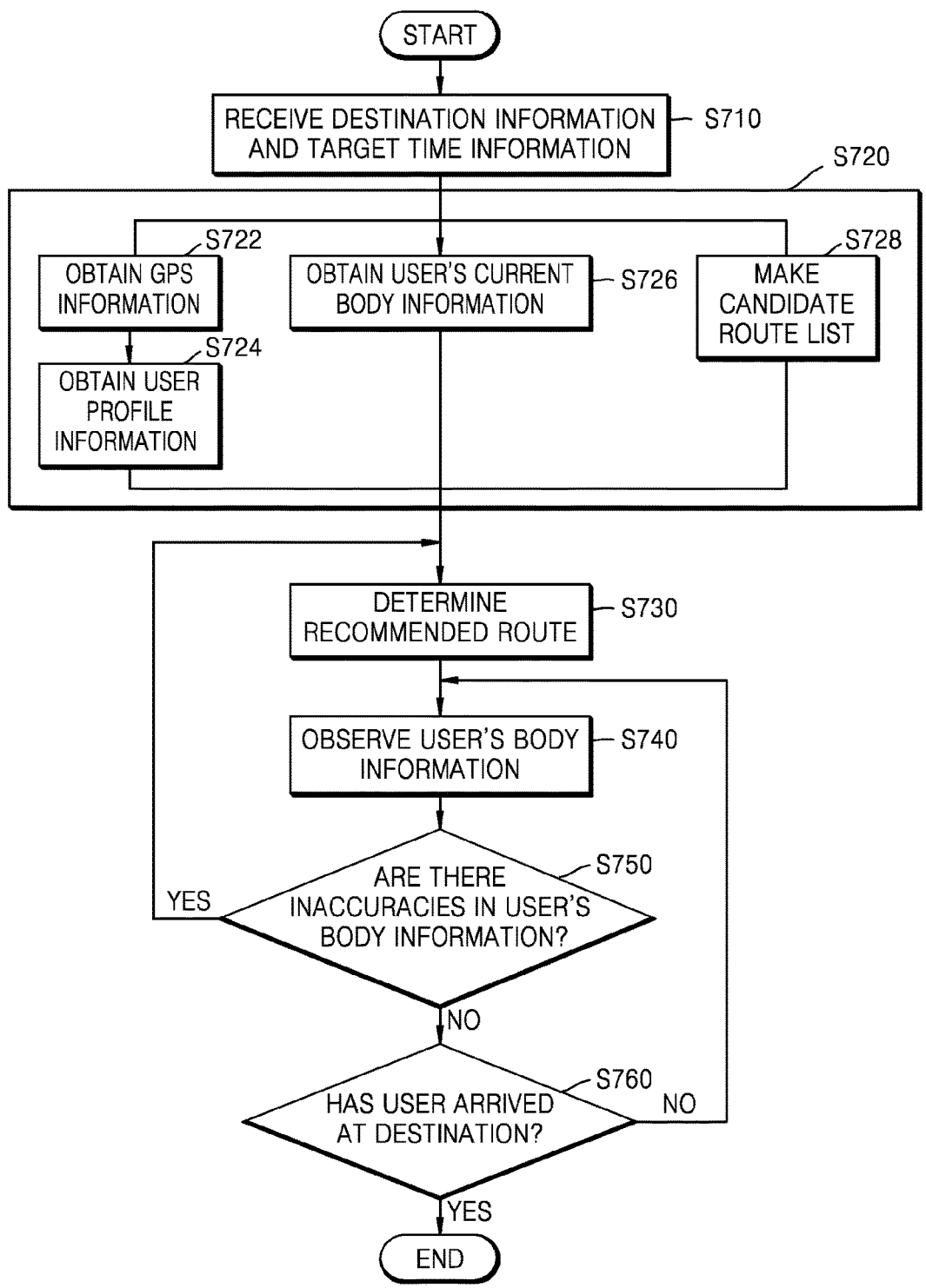
FIG. 7 is a flowchart illustrating a method of recommending a route, according to another embodiment of the present invention.

FIG. 7 illustrates a method of recommending a route, according to another embodiment of the present invention.

In step s710, a user selects destination information and target time information.

In step s720, information required to determine a recommended route is obtained.

In step s722, GPS information about a current position and a destination is obtained.

In step s724, user profile information is obtained.

In step s726, the user's current body information is obtained.

In step s728, a candidate route list is obtained on the basis of the GPS information.

In step s730, a recommended route is determined on the basis of the obtained information.

In step s740, route guidance according to the recommended route is performed, and at the same time, the user's body information is monitored in real time.

In step s750, it is determined whether an intersection exists or not, or whether there are inaccuracies in the user's body information. If the inspection determines that there are inaccuracies in the user's body information, step s730 is performed again to re-determine the recommended route. If it is determined that the intersection does not exist of there is no inaccuracy in the user's body information, step s760 is performed.

In step s760, it is determined whether a user has arrived at a destination. If the user has arrived at the destination, the route guidance is finished. If the user has not yet arrived at the destination, step s740 is repeatedly performed.

FIGS. 8A-8D illustrates interactions among a server, a mobile device and a wearable device according to an exemplary embodiment.

Figure 8A:
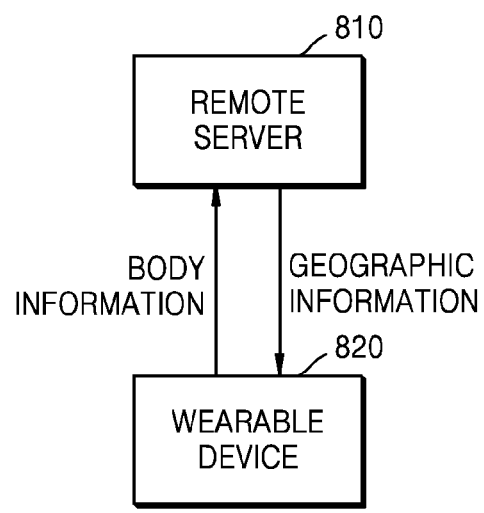
FIGS. 8A-8D illustrate interactions among a server, a mobile device and a wearable device, according to an embodiment of the present invention.
Figure 9:
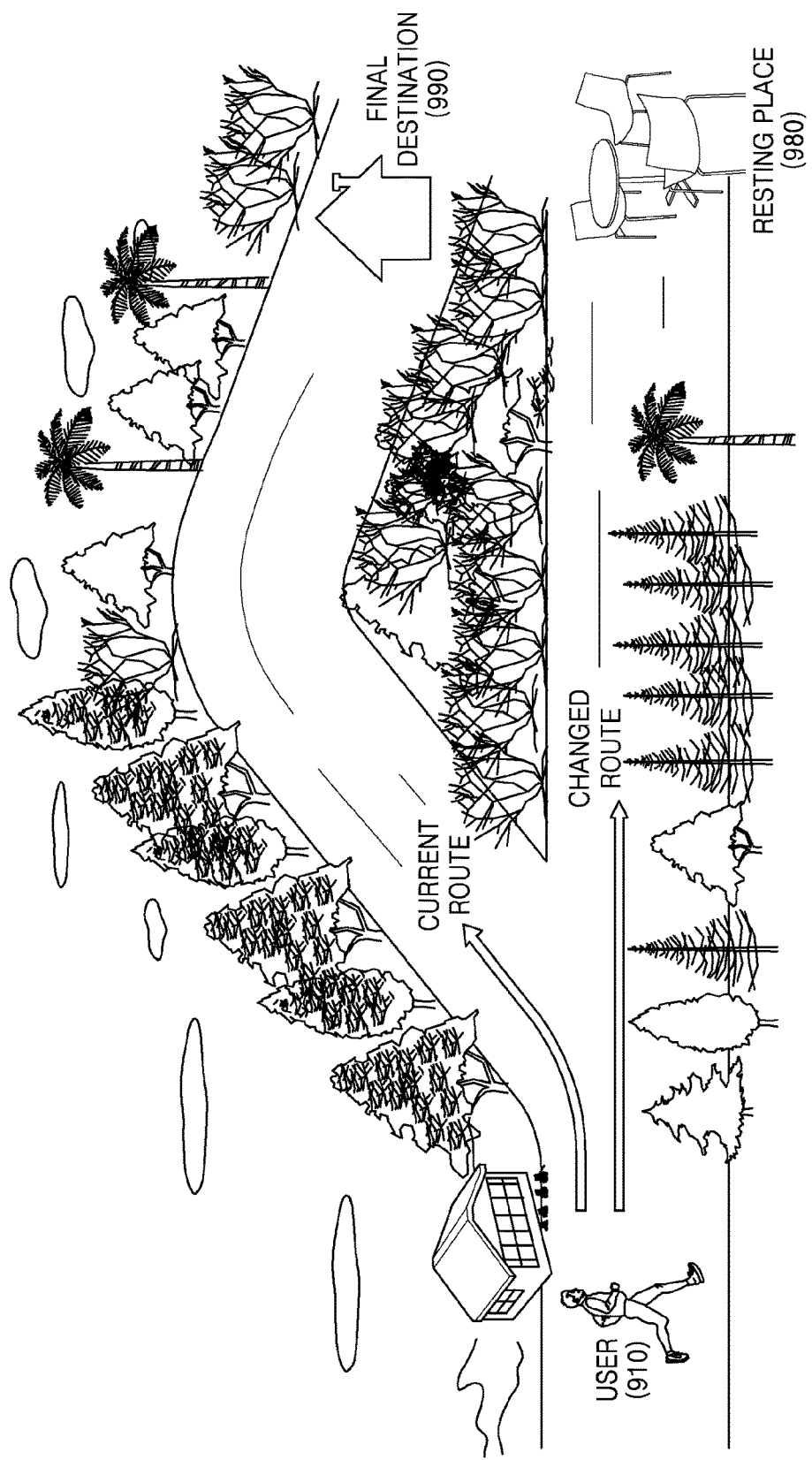
FIG. 9 illustrates how the user may change the original route or a destination based on the geographic information transmitted from a remote server, according to another embodiment of the present invention.

FIG. 8A illustrates interaction between a remote server 810 and a wearable device 820. The wearable device 820 is not limited to a wearable device but includes any type of portable device which can communicate with a remote server. The wearable device 820 may obtain body information as a result of checking a physical body condition and sensing certain indexes indicating the physical body condition. Referring to FIG. 9, such interaction will be more clearly described. For instance, while the user 910 of the wearable device 820 or a mobile device is heading toward a final destination 990, he or she may be sweating or his or her heart rate may have increased. The wearable device 820 may be able to check the body condition of the user by sensing various indexes such as brainwave activity, bone density index, caloric consumption, body temperature, amount of sweat and so forth. By way of checking the physical condition of the user 910 during the user's activities such as running, jogging or walking, the wearable device 820 can generate alert information if at least one of the indexes exceeds a predetermined threshold value. For example, if the heart rate exceeds 180 bpm, the wearable device 820 transmits the body information including the heart rate to the remote server 810. Further, when one of the indexes, for example, the heart rate, is above a predetermined threshold value, the wearable device 820 may analyze the index and determine that the user 910 needs to rest for a period. Accordingly, the wearable device 820 may send a request for a suitable rest location to the remote server 810. In response to the request, the remote server 810 may transmit the location of a nearby park and/or a rest area located on the route to the final destination 990. If such a place is not found on the route to the final destination, the remote sever 810 may send updated geographic information to the wearable device 820 and reroute the user to a rest location 980 located nearest the user's present location or alternately, the final destination 990. Based on the updated geographic information, the wearable device 820 may set the rest location 980 located nearest the final destination or the user's present location as a stopover location. In another embodiment, if the wearable device 820 determines that the user is sweating too much due to excessive exercise or physical activity, then geographic information may direct the user to any nearby convenience store to buy drinks. In another embodiment, if the wearable device 820 determines based on one of the indexes that the user is in a dangerous physical condition, the wearable device 820 may send a request for the location of an emergency treatment center and/or a drug store to the remote server 810. In response to the request, the remote server 810 may send the updated geographic information including the location of a hospital, a drug store and/or a nearby health center. In another example, the wearable device 820 may send a request for emergency treatment for the user, e.g., the wearable device 820 may request for an ambulance to be sent to the user's current location.

Figure 8B:
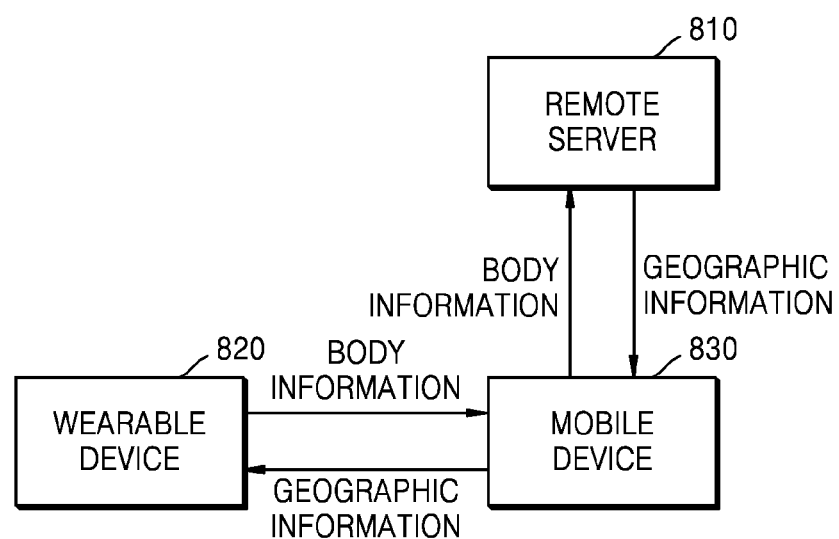

In another embodiment, FIG. 8B illustrates interactions between the remote server 810, a wearable device 820 and a mobile device 830. As shown in FIG. 8B, since the wearable device 820 and the mobile device 830 may be carried or worn at the same time by the user and may be wirelessly interconnected to each other, the wearable device 820 may transmit the body information to the mobile device 830 and receive geographic information from the remote server 810 via the mobile device 830. Often times, since the wearable device 820 is only able to communicate with devices over short distances, the mobile device 830, which can communicate with other devices over long distances, would interact with the remote server 810 on behalf of the wearable device 820.

Figure 8C:
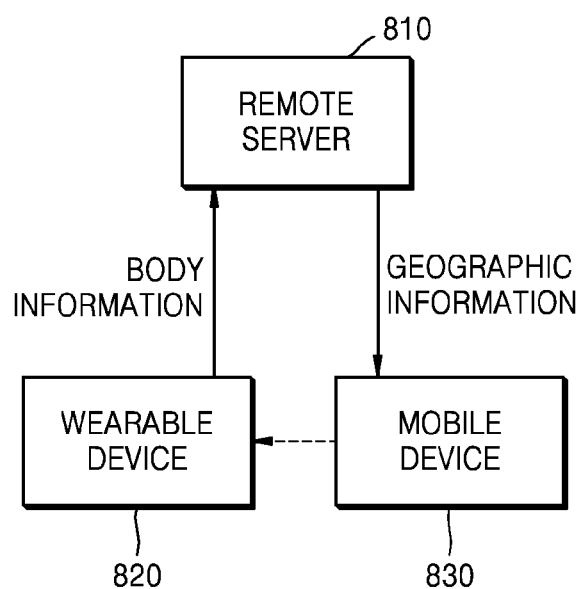

In another embodiment, as shown in FIG. 8C, in response to body information and a request for geographic information transmitted directly to the remote server 810 by the wearable device 820, the remote server 810 may transmit geographic information including a recommendation for changing a current route to the mobile device 830. As described earlier, the recommendation of changing the route includes changing a final destination and/or setting at least one stopover location based on the body information. In the event the display size of the mobile device 830 is larger than that of the wearable device 810, the user may choose to receive the geographic information for changing the route from the remote server 810 via the mobile device 830.

Figure 8D:
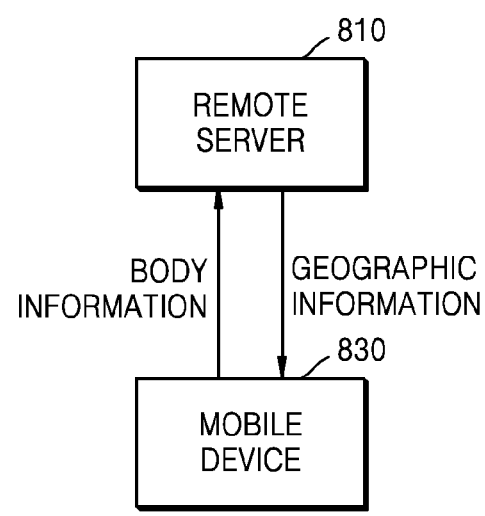

FIG. 8D shows another embodiment illustrating interaction between the mobile device 830 and the remote server 810. The mobile device 830 may transmit body information directly to the remote server 810 and receive geographic information directly from the remote server 810.

Figure 10:
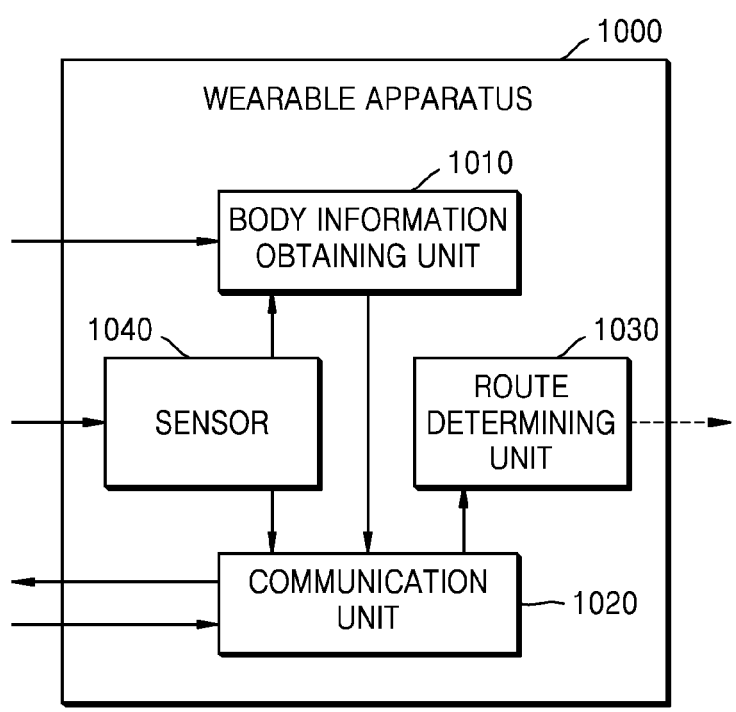
FIG. 10 illustrates a block diagram of a wearable apparatus, according to another embodiment of the present invention.

FIG. 10 illustrates a block diagram of a wearable apparatus 1000, according to another exemplary embodiment.

The wearable apparatus may include a body information obtaining unit 1010 which may obtain body information by sensing physical conditions of a user. As a result of sensing the physical conditions of the user, the wearable apparatus 1000 may obtain, as a part of the body information, indexes such as brainwave activity, bone density index, caloric consumption, body temperature and so forth.

If at least one of the indexes exceeds a predetermined threshold value, a communication unit 1020 may transmit the index or indexes as described above referring to FIG. 9. A remote server (not shown) may transmit geographic information to the communication unit 1020 in response to the index or indexes exceeding a predetermined threshold value and a route determining unit 1030 may change a predetermined route, thereby directing the user to another destination, based on the received geographic information and/or set at least one stopover location located on the way to the final destination. For example, based on the geographic information, the route determining unit 1030 may reroute the user to a destination different from the original destination and/or determine at least one stopover location located on the way to the final destination.

The wearable apparatus 1000 may be able to obtain the geographic information in various ways. For example, the wearable apparatus 1000 may obtain the geographic information from a remote server (not shown) via a mobile device (not shown) when the wearable apparatus 1000 is only capable of short range communication or the user of the wearable apparatus 1000 would like to reduce the data load on the wearable apparatus 1000 so that the wearable device 1000 only communicates with a predetermined mobile device (not shown) and the predetermined mobile device may communicate with the remote server (not shown). As a result, data may be forwarded to/from the wearable apparatus 1000 via the predetermined mobile device.

In another exemplary embodiment, the wearable apparatus 1000 may communicate with a remote server. In such an example, the communication unit 1020 may directly contact the remote server to transmit/receive data to/from the remote server.

In another exemplary embodiment, the wearable apparatus 1000 may be used to sense only the physical conditions of the user with a sensor 1040 and transmit the body information generated based thereon to the remote server. In this example, a mobile device would receive, from the remote server, geographic information generated based on the body information.

Figure 11:
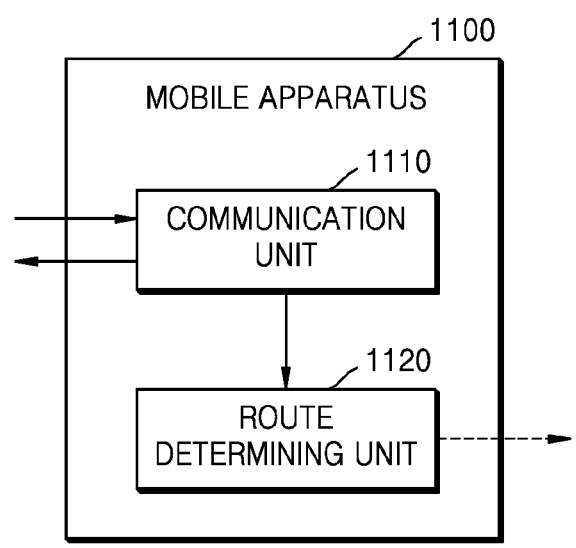
FIG. 11 illustrates a block diagram of a mobile apparatus, according to another embodiment of the present invention.

FIG. 11 illustrates a mobile apparatus 1100, according to another exemplary embodiment.

A communication unit 1110 included in the mobile apparatus 1100, may receive, from a wearable device (not shown), body information updated in accordance with a user's exercise or physical activity and transmit the body information along with a request for a location matching the body information to a remote server (not shown).

In response to the body information and the request, the remote server may generate geographic information to guide the user along a route different from an existing route, for example, to a destination different from a current destination. For example, the communication unit 1110 may receive the generated geographic information and a route determining unit 1120 may change the route and/or a final destination based on the generated geographic information. Alternatively, the communication unit 1110 may forward the geographic information to the wearable device so that the user of the wearable device can change the route by choosing a destination or a final destination or determine and set at least one stopover location before reaching the final destination.

Figure 12:
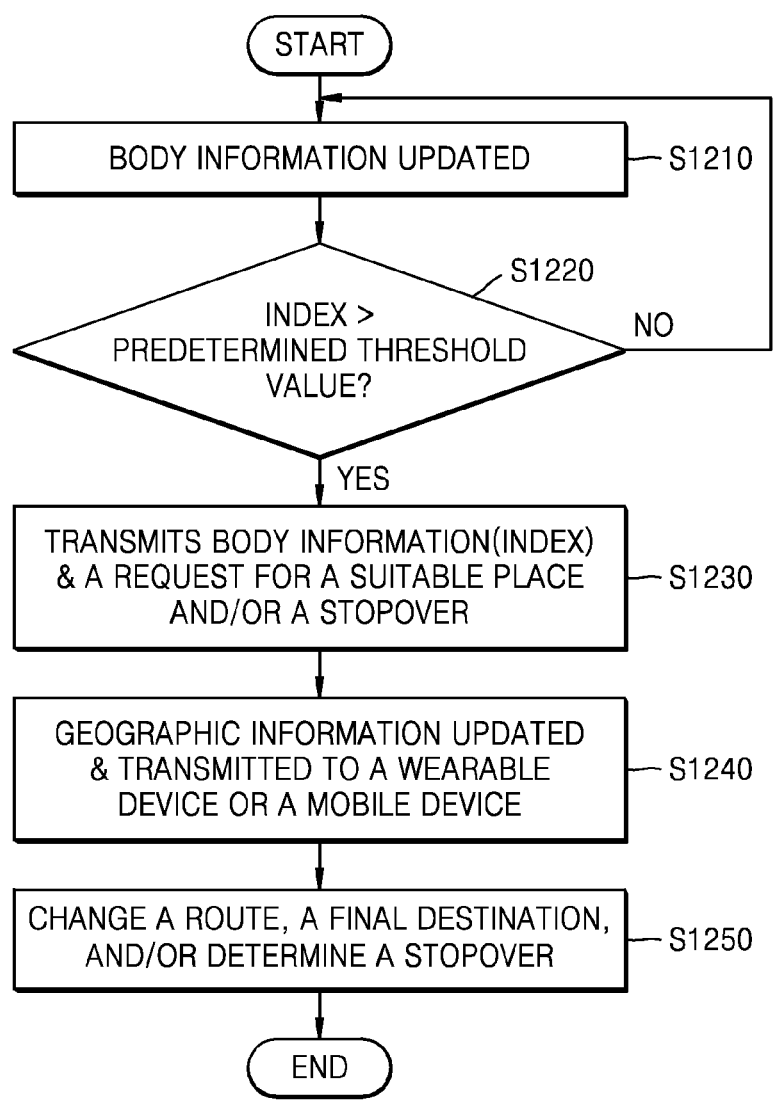
FIG. 12 is a flowchart illustrating a method of changing a route, according to another embodiment of the present invention.

FIG. 12 is a flowchart illustrating a method of changing a route according to another exemplary embodiment.

In step s1210, body information is updated in accordance with a user's exercise or physical activity such as jogging, running, or walking while heading for a destination.

In step s1220, a device carried by the user may determines whether at least one of the sensed indexes representing the physical condition of the user exceeds a predetermined threshold value, and then in step s1230, for any of the sensed indexes (a part of body information) exceeding a predetermined threshold value, said index and a request for a location matching the index (body information) are transmitted to a remote server or a mobile device. In the above-noted situation, the mobile device may ultimately transmit the received data to the remote server.

In step s1240, in response to the index (a part of body information) and the request, the remote server updates and generates geographic information which includes a suitable location matching the index (body information), the suitable location being located on the route to the user's final destination. Alternatively, the geographic information may be generated to change the final destination to another destination in accordance with the index (a part of body information) and the request.

In step s1250, after receiving the geographic information, the device carried by the user displays a map indicating the new final destination and/or any stopover location such as a hospital, a drug store, a health center, resting place, a restroom, a convenience store, a rest area and/or the user's house.

The present invention can also be embodied as computer readable codes on a computer readable recording medium. The computer readable recording medium is any non-transitory data storage device that can store data which can be thereafter read by a computer system. Examples of the computer readable recording medium include read-only memory (ROM), random-access memory (RAM), CD-ROMs, magnetic tapes, floppy disks, optical data storage devices, and etc. The computer readable recording medium can also be distributed over network-coupled computer systems so that the computer readable code is stored and executed in a distributed fashion.

While the present invention has been shown and described with reference to certain embodiments thereof, it will be understood by a person of ordinary skill in the art that various changes in form and details may be made therein without departing from the spirit and scope of the present invention as defined by the following claims. The described embodiments should be considered in a descriptive sense only and not for purposes of limitation. Therefore, the scope of the invention is defined not by the detailed description of the invention but by the claims. All differences within the scope are intended to be construed as embodiments of the present invention.

What is claimed is:

1. A method of changing a route in a wearable device worn on a body of a user, the method comprising:
    transmitting, from the wearable device, to a device, body information comprising at least one index indicating a physical condition of the user if the at least one index exceeds a predetermined threshold value due to the user's physical exercise;
    in response to the at least one index indicating the physical condition of the user, obtaining, from the device, geographic information including at least one stopover location matching the at least one index to address the physical condition;
    changing the route to a different route that includes the at least one stopover location before reaching the destination based on the geographic information; and
    outputting a route guide on a display indicating the destination and the at least one stopover location according to the changed route.

2. The method of claim 1, wherein the device is a remote server which stores the geographic information.

3. The method of claim 1, wherein transmitting the body information comprises directly transmitting the body information to a remote server and receiving the geographic information from the remote server via the device.

4. The method of claim 3, wherein the device is a mobile device enabled to communicate with the remote server.

5. The method of claim 1, wherein the at least one index comprises one of a heart rate, brainwave activity, bone density index, caloric consumption, body temperature, and amount of sweat.

6. The method of claim 5, wherein:
    transmitting the body information further comprises transmitting a request for a location if the at least one index exceeds the predetermined threshold value, and
    the received geographic information comprises information matching the request for the location.

7. The method of claim 6, wherein the received geographic information comprises location information of at least one of a hospital, a drug store, a health center, a restroom, a park, a rest area, and the user's house.

8. The method of claim 1, further comprising updating the body information if an intersection exists within a certain distance from a current position of the user.

9. A wearable apparatus worn on a body of a user for changing a route, the wearable apparatus comprising:
    a processor configured to
        control transmitting, to a device, body information comprising at least one index indicating a physical condition of the user, if the at least one index exceeds a predetermined threshold value due to the user's physical activity,
        obtain, from the device, in response to the at least one index indicating the physical condition of the user, geographic information including at least one stopover location matching the at least one index to address the physical condition, and
        change the route to a different route that includes the at least one stopover location before reaching a destination based on the geographic information; and
    a display for outputting a route guide indicating the destination and the at least one stopover location, according to the changed route.

10. The wearable apparatus of claim 9, wherein the device is a remote server which stores the geographic information.

11. The wearable apparatus of claim 10, wherein the processor controls transmitting the body information directly to the remote server and receives the geographic information from the server via the device.

12. The wearable apparatus of claim 11, wherein the device is a mobile device enabled to communicate with the remote server which stores the geographic information.

13. The wearable apparatus of claim 9, further comprising a sensor configured to sense the user's physical condition and generate the at least one index, wherein the at least one index portion of the body information comprises one of a heart rate, brainwave activity, a bone density index, caloric consumption, a body temperature, and an amount of sweat.

14. The wearable apparatus of claim 13, wherein the processor is further configured to controls transmitting, to the device, a request for at least one location if the at least one index exceeds the predetermined threshold value, and wherein geographic information comprises location information matching the request for the location.

15. The wearable apparatus of claim 14, wherein the location information comprises at least one of a hospital, a drug store, a health center, a restroom, a park, a rest area, and the user's house.

16. The wearable apparatus of claim 9, wherein the processor is further configured to update the body information if an intersection exists within a certain distance from a current position of the user.

* * * * *